United States Patent
Kydonieus et al.

(10) Patent No.: US 6,179,818 B1
(45) Date of Patent: Jan. 30, 2001

(54) OSTOMY BAGS AND VESSELS FOR BIOLOGICAL MATERIALS

(75) Inventors: Agis Kydonieus, Kendall Park; Cuilian Lin, Windsor; Kishore Shah, Bridgewater; Leslie Klem, Trenton, all of NJ (US)

(73) Assignee: Bristol-Myers Squibb Company, New York, NY (US)

( * ) Notice: Under 35 U.S.C. 154(b), the term of this patent shall be extended for 0 days.

(21) Appl. No.: 08/338,917

(22) Filed: Nov. 14, 1994

(51) Int. Cl.[7] .............................. A61F 13/15; A61B 19/00
(52) U.S. Cl. ........................ 604/332; 604/403; 604/408
(58) Field of Search ..................................... 604/332–338

(56) References Cited

U.S. PATENT DOCUMENTS

| | | | |
|---|---|---|---|
| 5,248,305 | * | 9/1993 | Zdrahala ............................... 604/280 |
| 5,468,803 | * | 11/1995 | Takahashi et al. ................... 524/553 |
| 5,496,295 | * | 3/1996 | Wilfong et al. ....................... 604/332 |

FOREIGN PATENT DOCUMENTS

0297741 * 1/1989 (EP) .
0405793 * 1/1991 (EP) .

* cited by examiner

Primary Examiner—John G. Weiss
Assistant Examiner—Carie Mager
(74) Attorney, Agent, or Firm—Theodore R. Furman, Jr.; John M. Kilcoyne (57) ABSTRACT

The invention provides a vessel for biological materials comprising a multilayer polymeric barrier material that has very low permeability to small molecules, such as water and oxygen, high flexibility and softness, and is resistant to tearing. The invention is particularly useful for forming vessels that receive biological fluids, such as ostomy bags and bags for storing blood, blood products, and IV solutions. The vessel comprises a flexible, multilayer, polymeric barrier material comprising (1) a first sandwich polymer layer, (2) at least one sandwiched, oriented liquid crystal polymer layer, and (3) a second sandwich polymer layer, the first and second sandwich layers disposed to sandwich the liquid crystal layer therebetween.

30 Claims, 4 Drawing Sheets

OSTOMY BAGS AND VESSELS FOR BIOLOGICAL MATERIALS

The invention relates to a vessel for biological materials comprising a multilayer polymeric barrier material that has very low permeability to small molecules, such as water and oxygen, high flexibility and softness, and is resistant to tearing. The invention is particularly useful for forming vessels that receive biological fluids, such as ostomy bags and bags for storing blood, blood products, and IV solutions. The barrier material is comprised of at least one layer of an oriented liquid crystal polymer ("LCP").

A critical feature for an ostomy bag, which is used to collect body fluids from the ostomies of colostomy, urostomy and ileostomy patients, is low oxygen permeability. The measure of oxygen permeability serves as a surrogate for measures of the permeability of other small molecules, such as those causing odor. The greater the oxygen permeability, it is believed, the more the ostomy bag will become a source of unpleasant odor as an ostomy patient's day progresses. In view of the odor problem, a material having an oxygen permeability in excess of about 100 $cc/m^2/day$ cannot reasonably be used for this purpose. A material that is now widely used commercially, a plasticized poly(vinylidene chloride) ("PVDC"), has a permeability of between about 35 $cc/m^2/day$ and 75 $cc/m^2/day$ when used in commercially practical thicknesses, (e.g., from about 10 to 75 $\mu$m). PVDC-based materials are sometimes plasticized to increase softness. However, plasticized materials generally must be thicker to provide adequate barrier properties.

PVDC-based materials are almost universally used despite the now well-established environmental concerns surrounding the use of chlorinated organic products. These concerns are especially accentuated for medical products, where biological safety issues make incineration, which can generate
dangerous chlorinated materials such as dioxin, a preferred method of disposal. The prevalence of PVDC-based products is based on their flexibility, softness and performance as odor barriers. One feature of the present invention is that it can be used to make a material with properties that make it practical for use in ostomy bags and that has an oxygen permeability substantially less than that of comparable PVDC films. In some embodiments, the present invention unexpectedly can show permeabilities of less than 5 $cc/m^2/$ day, even in some cases less than about 2 or about 1 $cc/m^2/day$, while retaining strength and flexibility properties suitable for forming ostomy bags.

Other properties that a material that forms an ostomy bag should have are strength, flexibility and softness. The importance of the strength of an ostomy bag to patients, for whom social environments can be trying, is self-evident. The importance of flexibility is less evident. Flexibility and softness correlate with quietness when the material is flexed. For instance, an ostomy bag of a sufficiently flexible material will not make a noise or "crinkle" when a patient moves or shifts his or her weight. The real or perceived social trauma arising from such noise can be substantial. With the present invention, it is believed that ostomy bags that at least match PVDC for strength, flexibility, softness and quietness can be prepared while retaining the remarkable barrier properties discussed above.

For vessels for IV solutions, blood and blood products, strength and flexibility have also been important properties. Safety issues accentuate the importance of strength. Flexibility is important for ease of handling and, more importantly, to allow the vessel to collapse when fluid is transferred out or to expand from a collapsed form when fluid is transferred into it. In this way, the collapsible vessel avoids the formation of vacuums or air pockets that would block fluid transfer. Biohazard safety is one of the reasons for using materials with good barrier properties for these vessels. Another function of the barrier properties of these vessels is to limit fluid loss. Traditionally, such bags have been constructed of poly(vinyl chloride) ("PVC"). PVC, while forming an excellent barrier to small molecules, nonetheless, when used by itself, allows the evaporation of too much water to be useful for long-term storage of such biological fluids. To overcome this, medical workers have typically used a second, enveloping bag of rubber-modified polyethylene to enclose the PVC bag and thus limit water loss. The barrier material of the present invention should limit this water loss, allowing medical workers to avoid using the second enveloping bag.

The combination of flexibility, strength and impermeance of the barrier material of the invention is surprising since the material has a core comprising an LCP. LCP materials have lately been recognized for their barrier properties, about which there has been interest in the food industry. See, e.g., Japanese Patent Applications Nos. 4135750, 3269054, 3071842, 2261456, 2253948–2253951, 2253920, 2220821, 2191636, 62187033, and 56028852, and European Patent Application No. 503063. However, it is believed that such materials have not been considered for use for forming the ostomy vessels and vessels for IV solutions, blood and blood products contemplated by the present invention. Such LCP compositions are notorious for their stiffness and the ease with which they tear along at least one axis. As discussed above, these properties would not be appropriate for the vessels of the invention. The present invention avoids the stiffness problem by using a thin layer of oriented LCP. (However, the thinness of the LCP layer, which has the greatest contribution to gas impermeability and a substantial contribution to strength, makes the superior performance of the invention over PVDC membranes even more surprising.

In one aspect, the present invention provides for increased tear resistance of the LCP layer by adding certain optically active compounds to the LCP material. Such optically active compounds can help bring about the formation of alignment patterns of the LCP materials to create a "cholesteric" phase (defined further below). Such cholesteric phases have multiple planar segments of aligned mesogenic groups, with the alignment of each succeeding planar segment incrementally offset from the alignment of the previous planar segment. The net result is that, for any direction of stress that might be applied to the material, there are aligned, self-reinforcing LCP molecules situated to meet the stress.

Another aspect of the present invention is to increase the tear resistance of the LCP layer by the application of torsional stress to the upper and lower surfaces of an LCP material as it is extruded from a slot die. The torsional stress tends to align the mesogenic groups in the LCP composition in the direction of the stress. The molecular alignment pattern of the upper, lower and even intermediate layers of material made this way can be such that there is sufficient reinforcement to meet stress along any axis, and thus to avoid tearing. See, Lusignea and Blizard, "Processing and Applications of Liquid Crystal Polymers and Blends, Society for Advancement of Material and Process Engineering" (1993).

Another method of increasing tear resistance in accordance with the present invention is to use the "inflation" method (also called the "blown film" process). See, Japanese Patent Application No. 4085325 and *Encyclopedia of Poly-*

*mer Science and Engineering* (John Wiley & Sons, 1987) V. 7, pp. 98–102. In this method, order in a first orientation is imposed by melt-extruding the LCP composition through a die. Concurrently, air is injected through the middle of the die, forming a bubble in the extruded material. The surface forces on the inflating film apparently impart new directions of order among some of the oriented, mesogenic domains. It is believed that film formed in this way has, within one layer, "biaxial" orientation. However, the applicant does not wish to be limited by this theory. The important observation is that films manufactured in this way have useful thicknesses for ostomy bags, as well as strength and odor barrier properties.

In another aspect of the present invention, the tear resistance of the LCP layer is increased by stretching an extruded LCP layer along an axis different from the extrusion axis. Typically, the LCP layer is stretched along the axis orthogonal to the extrusion axis.

SUMMARY OF THE INVENTION

The invention provides a vessel for biological materials comprising flexible, multilayer, polymeric barrier material comprising (1) a first sandwich polymer layer (2) at least one sandwiched, oriented liquid crystal polymer layer, and (3) a second sandwich polymer layer, wherein said first and second sandwich layers disposed to sandwich said liquid crystal layer therebetween.

One preferred embodiment of the invention provides a vessiel comprising a flexible, multilayer, polymeric barrier material as described above wherein each of the first and second polymer sandwich layers have a thickness of from about 15 $\mu$m to about 50 $\mu$m and the sandwiched, oriented liquid crystal polymer layers are nematic and have a total thickness of from about 5 $\mu$m to about 20 $\mu$m.

Figure 2:
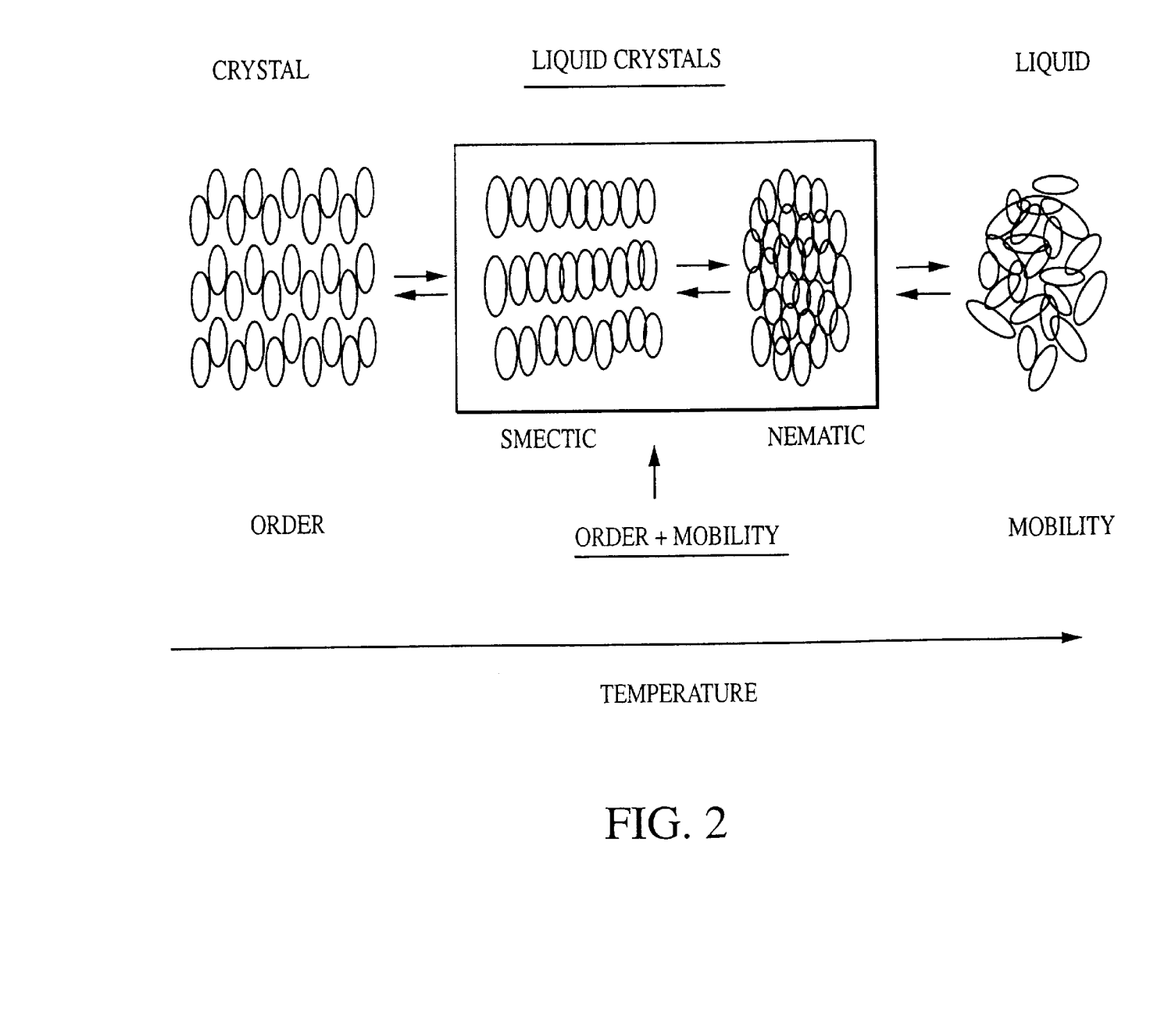
FIG. 2 illustrates the two major classes of liquid crystalline phases.

A liquid crystalline phase comprises an intermediate phase between the crystalline and the liquid phases. Compounds that can form such phases are typically rigid, rod-like or disk-like compounds (so-called "mesogens"). The molecules in a liquid crystalline phase are more organized than those in a isotropic liquid, but less organized than those in a true crystal. As illustrated in FIG. 2, two major classes of liquid crystalline phases, the smectic and nematic phases, have been identified. According to Ringsdorf, elt al. (*Angew.Chem.Int Ed.Engl.* (1988) 27:113–158), the molecules of a smectic phase have their "molecular domains organized in layers", while those of a nematic phase have "molecular domains distributed isotopically." These molecular domains are clusters of mesogenic groups. In a nematic phase, the longitudinal molecular axes of the mesogens of each molecular domain tend to orient parallel to each other.

Figure 3:
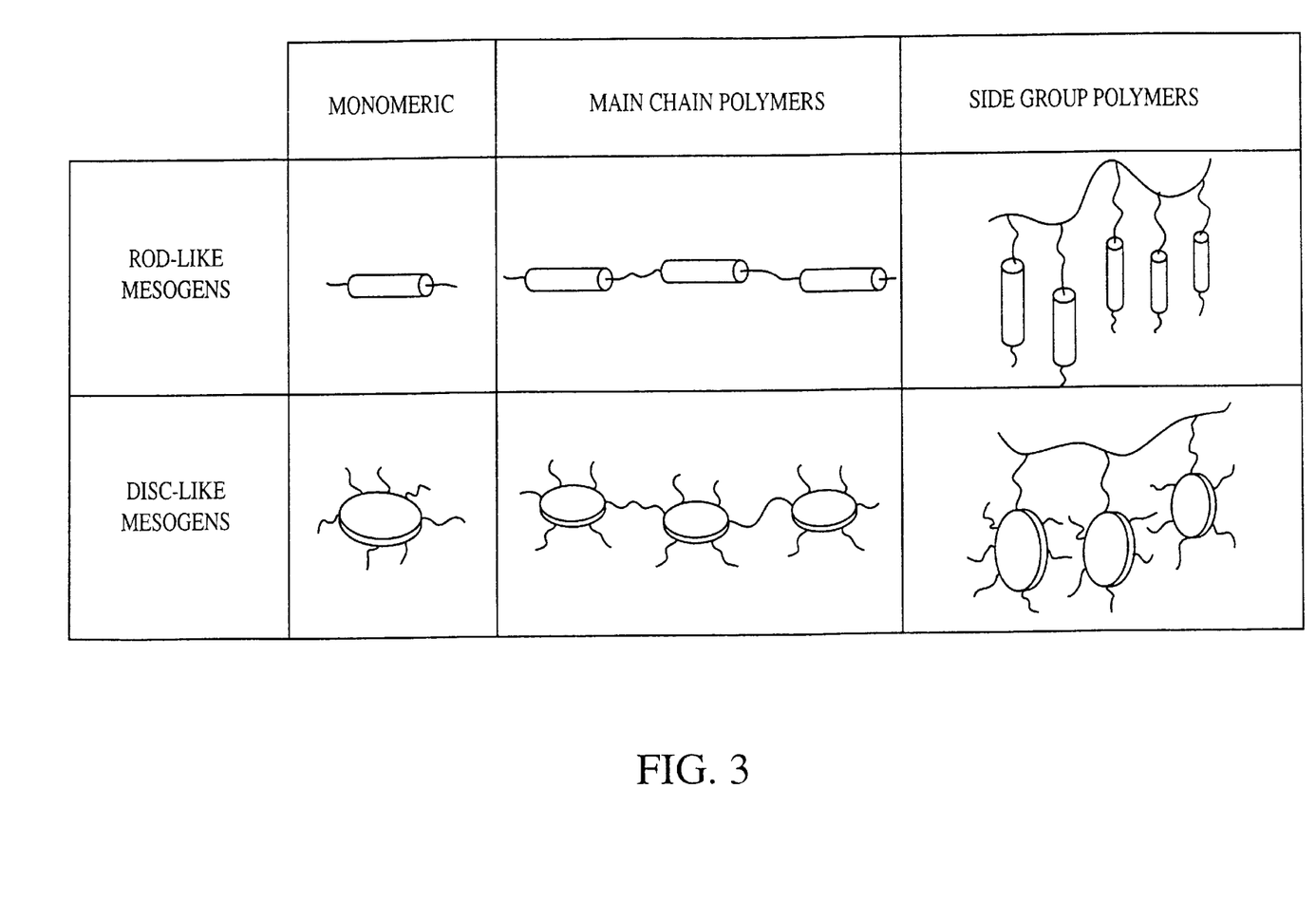
FIG. 3 illustrates the major classifications for LCPs.

The present invention involves polymeric mesogens, or liquid crystal polymers (LCPs). LCPs can be categorized into four classes: rod-like, main chain LCPs; rod-like, side group LCPs; disc-like, main chain LCPs; and disk-like, side group LCPs. These are illustrated in FIG. 3. These classes and variations thereof are described by Finkelmann, et al., "Liquid Crystal Polymers", *Liquid Crystals: Applications and Uses*, B. Bahadur, ed. (World Scientific, 1992), Vol. 3, p. 346.

In one aspect of the invention, the LCP layers of the barrier material will be oriented. This order can be described in terms of the orientation of the long axes of the mesogenic groups of the LCP molecules. The average orientation of the groups is often described by a vector called the director $\bar{n}$. See Madhusudana, "Theories of Liquid Crystals," *Liquid Crystals Applications and Uses*, Birendra Bahadur, ed. (World Scientific, 1990) Vol. 1, pp. 38–87. For the present purposes, the "long axis" is the axis about which the mesogenic group has the smallest moment of inertia. The degree of orientation can be defined in terms of an order parameter (S) as follows:

$$S = \left\langle \frac{3\cos^2\beta - 1}{2} \right\rangle,$$

where $\beta$ is the polar angle between the long axis of an individual mesogen and $\bar{n}$, and where the angular brackets indicate an average for all mesogens in a layer. Id. When S=1, there is perfect alignment with $\bar{n}$; when S=0, the composition as a whole is without order. In some aspects, the invention will be described in terms of the direction of the projection of $\bar{n}$, for any layer, onto the plane of the layer.

Figure 4:
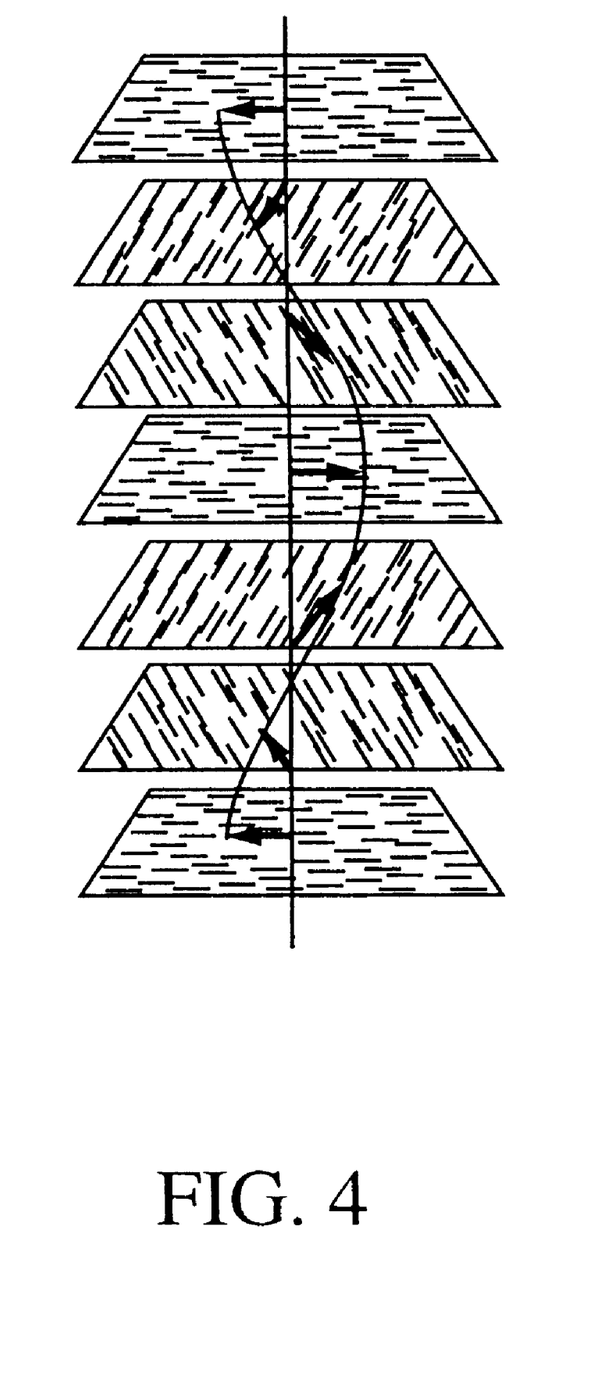
FIG. 4 illustrates the helical pattern of the director $\bar{n}$ of a cholesteric LCP phase.

There is another type of liquid crystal phase, the cholesteric phase, which is considered a subclassification of the nematic phase. For the purposes of this application, the term "nematic phase" shall encompass cholesteric phases. In cholesteric phases, there is a tendency for the mesogens in one portion of the phase to align along a given axis, while in an immediately adjacent portion the mesogens align along an axis that is incrementally offset from the first axis. Such phases have been termed "super twisted nematic" phases, and usually produce visible light refraction patterns. In films of cholesteric liquid crystals, one tends to see the layered organizations, where the projections of the directors $\bar{n}$ from an axis perpendicular to the film adopts a helical arrangement, as illustrated in FIG. 4. Cholesteric phases are typically created by using an appropriate optically active mesogen or by adding to a mesogen composition certain optically active compounds. The phase takes its name from the historical practice of using cholesterol or a derivative thereof as the optically active compound.

The LCPs to be used in the invention are preferably polymers with rod-like mesogenic moieties, particularly rod-like main chain polymers, although it is believed that other types of LCPs will prove useful in the invention.

Particularly preferred LCPs are the co-polyesters described by the formula:

wherein n and m are integers, and the co-polyester-amide described by the following formula:

wherein n' and m' are integers. These polymers are described in U.S. Pat. No. 4,161,470 and are produced and marketed by Hoechst Celanese (Chatham, N.J.; Greer, S.C.) under the tradename Vectra®. Other useful LCPs are available from Amoco Performance Products, Inc. (Alpharetta, Ga.) under the tradename Xydar® or from the Du Pont Co., (Wilmington, Del.) under the tradenames HX6000 and HX7000. Mixtures of LCPs should also be useful. Typically, the copolyesters and copolyester-amides described above have a coefficient of thermal expansion of about 2 ppm/° C. to about 10 ppm/° C. in the flow direction preferably about 5 ppm/° C., and about 30 to about 50 ppm in the traverse direction. The melt point for these polymers will typically be between about 240° C. and about 340° C., more typically between about 280° C. and about 325° C.

The LCP layer of the present invention need not be comprised solely of LCP molecules. The amount of LCP required will vary with the LCP and filler used. Generally, however, an LCP content of at least 2% is preferred; a content of at least 3% is more preferred. Those of ordinary skill in polymer sciences will recognize that numerous structural fillers may be used, including glass fibers, mineral resins, graphic flakes, non-LCP polyesters and polyamides, and other polymers. As is typically the case for polymer blends, some of these blends will prove incompatible at some or all blend ratios. However, the parameters of such incompatibilities are routinely examined by polymer chemists and will not prove an obstacle to practicing the invention. Similarly, blend ratios that produce LCP layers that are less effective in terms of strength, flexibility, softness or permeability can readily be identified in light of the present disclosure. See, for example, the test procedures published by the American Society for Testing and Materials. Other fillers, including plasticizers and colorants, may also be added.

Preferably, for most applications including the formulation of ostomy bags, the total thickness of the sandwiched LCP layers will range frorm about 5 $\mu$m to about 50 $\mu$m; more preferably the range will be between about 5 $\mu$m and about 25 $\mu$m; still more preferably the range will be between about 5 $\mu$m and about 15 $\mu$m. For LCP materials with high levels of plasticizer (generally, about 1% to about 6% by weight), the total thickness of the LCP layers will generally need to be in the high end of these ranges to achieve satisfactory barrier properties.

At least one of the LCP layers will be oriented. Such ordering can be imposed by adding a cholesteric agent to form a cholesteric phase. Under such circumstances, films of cholesteric LCP will have a large number of planar segments where the LCPs have an identifiably different alignment. See, for instance, the cholesteric material diagrammed in FIG. 4.

Another way to impart order to films of LCPs is to apply a directional stress to the surface of the LCP material. Such directional stress tends to orient the LCP molecules of the material, the effect being greater the closer the LCP molecule is to the surface of the material. This method is particularly effective when the stress is applied while the material is being formed by die extrusion. Blumstein, *Polymer News*, 5:254–261 (1979); Lorkowksy and Reuther, *Plaste Und Kautschuk*, 23:81 (1976); Lusignea and Blizard, "Processing and Applications of Liquid Crystal Polymers and Blends," Society for Advancement of Material and Process Engineering (1993). The method has even been used to impart biaxial orientation order to LCP materials. Biaxial orientation is preferred since it is believed to impart greater sheer strength onto the film.

To impart shear strength to thinner films, the inflation method has been used (as discussed above). See, for example, Japanese Patent Application No. 4085325. It is believed that such methods can produce films with biaxial orientation order in a single layer. Whatever the mechanism, however, the inflation method creates films with strength and good odor barrier properties. By this method, useful films of thicknesses generally greater than about 12 $\mu$m can be manufactured.

One dimensional orientation can be imparted to a film during die extrusion. In such films, the direction of orientation of the mesogenic domains is the machine direction, that is, the direction of extrusion. To impart greater shear strength, the film can then be stretched in another direction. Generally, the film is stretched along an axis that is about 40 degrees to about 90 degrees offset from the machine direction, preferably, preferably about 70 to about 90 degrees, more preferably, about 90 degrees. The film is generally stretched with a roller process until it has expanded at least about 2%, preferably at least about 5%. Of course, the amount of stretching that will be practical and desirable will vary with the thickness of the extruded film; Thinner films will generally be stretched less than thicker films. The stretching process is generally applied directly after extrusion when the film is in a melt or rubbery state. See, *Encyclopedia of Polymer Science and Engineering* (John Wiley & Sons, 1987), Vol. 7., p. 98. It is believed that this stretch method systematically alters the direction of a subpopulation of mesogenic domains. The result being a film that has biaxial orientation. However, whatever the mechanism, it has been observed that films that have been so manufactured have excellent strength. It is believed that this method can be used to make LCP films of thicknesses from about 5 $\mu$m to about 75 $\mu$m.

Additional oriented layers can be incorporated into the flexible, barrier material by laminating films of oriented LCPs. For instance, one of two equivalent oriented LCP films can be rotated with respect to the other and laminated. By this method, the number of oriented layers and alignment axes can be increased. Laminated layers can be produced, for instance, by calendering films, preferably with an adhesive (or "tying") layer interposed between the two LCP films, or by heat lamination. Suitable adhesive layer compositions include poly(ethylene vinyl acetate) ("EVA"), polyurethane (for example, two-component adhesives such as Adcote 710 A&C™, sold by Morton Thiokol), polyethylene acrylic acid and acrylic hot melt adhesive. Laminates can also be produced by co-extrusion. Alternatively, one film can be extruded onto a pre-formed film, especially where differences in the thermal coefficients of expansion of the films preclude co-extrusion.

Generally, unidirectionally oriented LCP layers will have order. parameters of at least about 0.01. Order parameters may be estimated by optical methods. See, V. P. Shibayer et al., Polymer Science, U.S.S.R., 32:2384–2428 (1990). When the flexible, barrier material has at least two unidirectionally aligned LCP layers, the projections of $\overline{n}$ (for each of the two layers) onto the plane of its layer will generally be offset by at least about 10 degrees.

The sandwich polymer layers will preferably be comprised of a thermoplastic polymer of low hygroscopicity (i.e., a hydrophobic polymer). Preferably the polymers will absorb (at equilibrium, under 70% relative humidify, and at 25° C.) no more than about 5% w/w of water. More preferably, the equilibrium water content is no more than about 2% w/w in 24 hours. Preferably, the thermoplastic polymer of at least one of the sandwich layers will be suitable for heat sealing, ultrasonic sealing or $R_f$ sealing. Suitable thermoplastic polymers for use in the sandwich layers include EVA, low density polyethylene, polyurethane, chlorinated polyethylene, polyvinyl chloride, polyamide, thermoplastic polyester and mixtures thereof. EVA with up to about 18% vinyl acetate content (e.g. Elvax 410™, from Du Pont Co., Wilmington, Del.) is particularly suitable. Generally, the vinyl acetate content will not be more than bout 45%, or the EVA will be too soft and difficult to work with.

For ostomy bags, generally, the thickness of each of the sandwich layers shall range from between about 10 $\mu$m and about 80 $\mu$m. Preferably, the thickness of the sandwich layers will be between about 10 $\mu$m and about 50 $\mu$m; more preferably, the thickness will range from about 15 $\mu$m to about 40 $\mu$m; still more preferably, the thickness will range from about 20 $\mu$m and about 30 $\mu$m. When the flexible polymer barrier material is to be used to form bags for I.V. solutions, blood or blood products, the thickness of the sandwich layers will generally be between about 50 $\mu$m and about 300 $\mu$m; preferably, the thickness will be between about 100 $\mu$m and about 200 $\mu$m; more preferably, the thickness will be between about 125 $\mu$m and about 175 $\mu$m.

The sandwich layers may be applied to the LCP by coextrusion or solution coating. Alternately, one layer may be applied to a preformed layer by extrusion, especially where differences in the thermal coefficient of expansion for the sandwich and the LCP layers preclude coextrusion.

Figure 1:
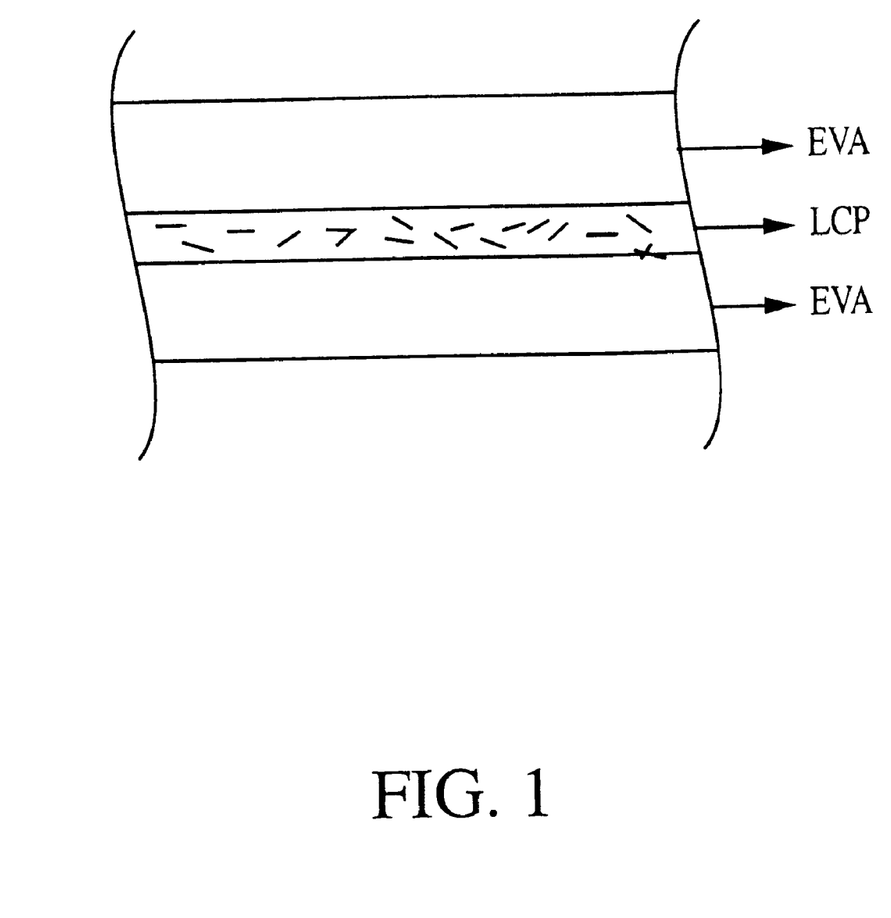
FIG. 1 displays a cross-section of a preferred embodiment of the flexible, multilayer, polymeric barrier of the invention.

An embodiment of the multilayer, polymeric barrier material is illustrated in FIG. 1.

The flexible, multi-layer, polymeric barrier material of the invention should possess an oxygen permeability of no more than about 50 cc/m$^2$/day. Generally the barrier material will possess an oxygen permeability of no more than about 10 cc/m$^2$/day; preferably, the oxygen permeability will be no more than about 5 cc/m$^2$/day. Oxygen permeabilities of less than about 3, 2 or about 1 cc/m$^2$/day have been demonstrated and are, of course, still more preferred.

The flexible, multi-layer, polymeric material of the invention will preferably have a tensile strength of at least 2,000 psi.

The flexibility, softness or quietness of materials of the invention will preferably be at least as good a that of a comparison barrier material made of a laminate of low density polyethylene/PVDC/low density polyethylene with layer thicknesses of 30 $\mu$m/10 $\mu$m/30 $\mu$m. Such a comparative material is commercially available, as Savanex 40™, from Dow Chemicals (Midland, Mich.). More preferably, the materials of the invention will be superior to this comparative material in flexibility, softness or quietness.

Flexibility, softness or quietness are best assessed by using panels of people who are without knowledge of the brand or composition of the materials they are asked to compare. Such panels, it is believed, will identify materials of the invention as equal to, or superior, to the comparative material in flexibility, softness or quietness. Preferably, the size of such panels will be sufficient to allow for statistical assessments of the panels' determinations.

A more quantitative measure that correlates with softness is the elastic modulus (i.e., Young's modulus). See Schael, *Medical Plastics and Biomaterials* (Fall 1994), pp. 12–18. Generally, the multilayer barrier material will have an elastic modulus of between about 40,000 psi and about 500,000 psi, preferably between about 40,000 psi and 100,000 psi and/or at least about the same or less than that of the comparative PVDC material identified above.

The construction of the vessels of the invention may require consideration of parameters not described herein. For instance, an ostomy bag should have a resilient face plate that reversible attaches to a face plate fitted on the ostomy. However, these parameters are well understood by those practicing the art, and they are not the focus of the present invention. For ostomy bags, such parameters are described in U.S. Pat. Nos. 4,465,486, 4,490,145, 4,460,363 and 4,826,493.

The invention is illustrated by the non-limiting examples described below. From the data described in the examples, it is clear that barrier materials according to the invention can have oxygen permeabilities that are substantially less than those of PVDC-based ostomy bag materials. The barrier materials according to the invention are thicker than the comparative material. However, it is the LCP layer that has the greatest contribution to the barrier properties of the material. Thus, it is significant that materials with LCP layers of no more than 25 $\mu$m thickness are extremely effective as oxygen barriers.

EXAMPLE 1

A 21 cm by 27 cm sheet of 51 $\mu$m thick VECTRAN® film (Hoechst Celanese, Greer, S.C.), having at least one unidirectionally oriented layer of poly(benzoate-naphthalate), was used to form a barrier material according to the invention. The film was coated on both sides with an ethyl acetate solution of EVA (Elvax 40 W, DuPont, Wilmington, Del.). The coated film was dried under vacuum overnight to remove the ethyl acetate carrier solvent. The total thickness of the resulting material was 178±25 $\mu$m. The oxygen permeability of the material and that of PVDC-based material was compared at 23° C. using a MOCON OX-TRAN 200 permeability tester (Modern Controls Inc., Minneapolis, Minn.). The comparative ostomy bag material MF373™ (WR Grace, Columbia, Md.) was a three-layer laminate, having a center layer of PVDC and sandwich layers of EVA. The results were as follows:

TABLE 1

| | OXYGEN PERMEATION | | |
|---|---|---|---|
| FILM NAME | AREA (cm$^2$) | THICKNESS ($\mu$m) | PERMEABILITY (cc/m$^2$/day) |
| EVA/LCP/EVA | 50 | 178 | 0.6500 |
| MF373 | 50 | 75 | 35 |

EXAMPLE 2

Another barrier material was constructed using a 25 $\mu$m thick film of VECTRAN® film. EVA was coated onto the film by the same methodology described above to create a material with a thickness of 102±25 µm. This material, and the material tested in the previous examples were compared for oxygen permeability as follows:

TABLE 2

OXYGEN PERMEATION

| FILM NAME | AREA (cm$^2$) | THICKNESS (Total/LCP) (µm) | PERMEABILITY (cc/m$^2$/day) |
|---|---|---|---|
| EVA/LCP/EVA | 50 | 102/25 | 0.7300 |
| EVA/LCP/EVA | 50 | 178/51 | 0.6500 |
| MF373 | 50 | 75/— | 35 |

What is claimed is:

1. A collection vessel to receive and contain body wastes, IV solutions, blood, blood products and other biological materials, wherein said collection vessel is made of sheets of a flexible, multilayer, polymeric barrier material comprising
   (1) a first sandwich polymer layer,
   (2) at least one sandwiched, oriented liquid crystal polymer layer, and
   (3) a second sandwich polymer layer,
wherein said first and second sandwich layers are disposed to sandwich said liquid crystal polymer layer therebetween.

2. The collection vessel of claim 1 wherein liquid crystal polymer molecules of at least one of said layers are substantially aligned with one another, defining a director $\bar{n}_1$, and forming a first aligned liquid crystal polymer layer.

3. The collection vessel of claim 2, wherein the order parameter (S) of the first aligned layer is at least 0.01.

4. The collection vessel of claim 3 wherein said flexible barrier material comprises at least a second sandwiched liquid crystal polymer layer, wherein liquid polymer molecules of the second liquid crystal polymer layer are substantially aligned with one another, defining $\bar{n}_2$ wherein the order parameter ($S_2$) parameter of the second aligned layer is at least 0.01.

5. The collection vessel of claim 4 wherein the projections of $\bar{n}_1$ and $\bar{n}_2$ onto the plane of their respective layers have an angular offset of at least 10 degrees.

6. The collection vessel of claim 1 wherein each of said first and second sandwich layers comprises a hydrophobic polymer.

7. The collection vessel of claim 6 wherein each said hydrophobic polymer absorbs no more than 5% w/w water at equilibrium at 25° C. under 70% relative humidity.

8. The collection vessel of claim 7 wherein each said hydrophobic polymer absorbs no more than 2% w/w water at equilibrium at 25° C. under 70% relative humidity.

9. The collection vessel of claim 1 wherein the liquid crystal polymer layer comprises a nematic liquid crystal polymer and the total layer thicknesses,) of the sandwiched one or more liquid crystal polymer layers and of the sandwich layers are selected to provide flexibility for said barrier material.

10. An ostomy bag made of sheets of a multilayer, polymeric barrier material comprising
   (1) a first sandwich polymer layer,
   (2) at least one sandwiched, oriented liquid crystal polymer layer, and
   (3) a second sandwich polymer layer,
wherein said first and second sandwich lavers are disposed to sandwich said liquid crystal polymer layer therebetween, said liquid crystal polymer layer comprises a nematic liquid crystal polymer, and the total layer thicknesses of the sandwiched one or more liquid crystal polymer layers and of the sandwich layers are selected to provide flexibility for said barrier material.

11. The ostomy bag of claim 10 wherein the first and second sandwich layers independently have thicknesses between about 10 µm and about 50 µm, and the total thickness of the one or more liquid crystal polymer layers is between about 5 µm and about 50 µm.

12. The ostomy bag of claim 11 wherein the sandwich layers have thicknesses between about 15 µm and about 40 µm, and the total thickness of the one or more liquid crystal polymer layers is between about 5 µm and about 25 µm.

13. The ostomy bag of claim 12 wherein the sandwich layers have thicknesses between about 20 µm and about 30 µm, and the total thickness of the one or more liquid crystal polymer layers is between about 5 µm and about 15 µm.

14. The collection vessel of claim 9 wherein the vessel is a collection vessel for IV solutions, blood or blood products.

15. The collection vessel of claim 14 wherein the vessel is a collection vessel for IV solutions.

16. The collection vessel of claim 14 wherein the vessel is a collection vessel for blood or blood products.

17. The collection vessel of claim 14 wherein the sandwich layers independently have thicknesses between about 50 µm and about 300 µm and the total thickness of the one or more liquid crystal polymer layers is between about 5 µm and about 50 µm.

18. The collection vessel of claim 17 wherein the sandwich layers independently have thicknesses between about 100 µm and about 200 µm and the total thickness of the one or more liquid crystal polymer layers is between about 5 µm and about 25 µm.

19. The collection vessel of claim 18 wherein the sandwich layers independently have thicknesses between about 100 µm and about 200 µm and the total thickness of the one or more liquid crystal polymer layers is between about 5 µm and about 15 µm.

20. The collection vessel of claim 9 wherein said flexible barrier material is at least as soft and quiet as a 30 µm/10 µm/30 µm sandwich laminate of low density polyethylene sandwich layers and a PVDC core layer.

21. The collection vessel of claim 20 wherein said flexible barrier material has an oxygen permeability of no more than 5/cc/m$^2$/day.

22. The collection vessel of claim 21 wherein said flexible barrier material has an oxygen permeability of no more than 2/cc/m$^2$/day.

23. The collection vessel of claim 21 wherein said flexible barrier material has an oxygen permeability of no more than 2/cc/m$^2$/day.

24. The collection vessel of claim 21 wherein said liquid crystal polymer layer comprises a liquid crystal polymer selected from the group consisting of aromatic polyamide liquid crystal polymers, aromatic copoly(ester-amides) liquid crystal polymers, and mixtures thereof.

25. The collection vessel of claim 24, wherein said sandwich layers comprise a polymer selected from the group consisting of EVA, low density polyethylene, polyurethane, chlorinated polyethylene, polyvinyl chloride, polystyrene, polyamide, polyacrylonitrile, thermoplastic polyester and mixtures thereof.

26. The collection vessel of claim 1, wherein at least one of said liquid crystal polymers layers is manufactured by stretching a film having orientation that defines a director $\bar{n}$, along a direction different from the direction of the projection of $\bar{n}$ onto the plane of the film.

27. The collection vessel of claim 22 wherein the total layer thicknesses of the sandwiched liquid crystal polymer layer(s) and of the sandwich layers are selected to provide flexibility for said barrier material.

28. The collection vessel of claim 27 wherein the vessel is an ostomy bag, and the first and second sandwich layers each have thicknesses between about 10 μm and about 50 μm, and the total thickness of the one or more liquid crystal polymer layers is between about 5 μm and about 50 μm.

29. The collection vessel of claim 27 wherein the vessel is a vessel for IV solutions, blood and blood products and the first and second sandwich layers each independently have thicknesses between about 100 μm and about 200 μm and the total thickness of the one or more liquid crystal polymer layers is between about 5 μm and about 50 μm.

30. A method of collecting exudates from an ostomy which reduces the odors usually associated with such procedures comprising:

provyiding a collection vessel for ostomy exudates such as feces and urine comprising sheets of
  (1) a first sandwich polymer layer
  (2) at least one sandwiched, oriented, liquid crystal polymer layer, and
  (3) a second sandwich polymer layer, wherein said first and second sandwich layers are disposed to sandwich said liquid crystal layer therebetween; and attaching said collection vessel to said ostomy, whereby said exudates may exude from said ostomy and collect in said vessel while separated from the outside environment by said barrier material.

\* \* \* \* \*